United States Patent [19]

Wallace et al.

[11] Patent Number: 5,795,961
[45] Date of Patent: Aug. 18, 1998

[54] RECOMBINANT HUMAN ANTI-LEWIS B ANTIBODIES

[75] Inventors: T. Paul Wallace, Aberdeenshire; William J. Harris, Carnoustie; Frank J. Carr, Balmedie, all of Great Britain; Lloyd J. Old, New York; Sydney Welt, Armonk, both of N.Y.; Kunio Kitamura, Nagoya, Japan

[73] Assignee: Ludwig Institute for Cancer Research, New York, N.Y.

[21] Appl. No.: 388,672

[22] Filed: Feb. 14, 1995

[51] Int. Cl.⁶ .................. C07K 14/00; A61K 38/16; C12P 21/08

[52] U.S. Cl. .................. 530/350; 530/380; 530/386; 530/387.3; 530/387.7; 530/388.1; 530/388.2; 530/388.8; 530/388.85

[58] Field of Search .................. 530/350, 380, 530/386, 387.3, 387.7, 388.1, 388.2, 388.8, 388.85

[56] References Cited

U.S. PATENT DOCUMENTS 4,607,009   8/1986   Steplewski et al.

OTHER PUBLICATIONS

Suhl (S. Histochem. Cytochem 33:309–314), 1985.

*Primary Examiner*—Lila Feisee
*Assistant Examiner*—Susan Ungar
*Attorney, Agent, or Firm*—Felfe & Lynch

[57] ABSTRACT

The invention provides for the production of several humanized murine antibodies specific for the Lewis b antigen, which is recognized by the murine antibody 58-1066. The antigen is expressed on cell lines from colon, lung, bladder, breast, renal, pancreatic and ovarian cancers. The expression of the antigen is greatly increased in cancer tissues as compared to its expression in the corresponding normal tissue. The invention also provides for numerous polynucleotide encoding humanized Lewis b antigen specific antibodies, expression vectors for producing humanized Lewis b antigen specific antibodies, and host cells for the recombinant production of the humanized antibodies. The invention also provides methods for detecting cancerous cells (in vitro and in vivo) using humanized Lewis b antigen specific antibodies. Additionally, the invention provides methods of treating cancer using Lewis b antigen specific antibodies.

5 Claims, 4 Drawing Sheets

```
CAGGTSMARCTGCAGSAGTCWGGAGCTGAGCTGGTAAGGCCTGGGACTTC
----.----+----.----+----.----+----.----+----.----+   50
GTCCASKTYGACGTGSTCAGWCCTCGACTCGACCATTCCGGACCCTGAAG q   v  k/q  l  q d/h  s   g   a   e   l   v   r   p   g   t   s
----.----+----.----+----.----+----.----+----.----+

AGTGAAGATGTCCTGCAAGGCTGCTGATTACACCTTCACTAGCTACTGGA
----.----+----.----+----.----+----.----+----.----+   100
TCACTTCTACAGGACGTTCCGACGACTAATGTGGAAGTGATCGATGACCT v   k   m   s   c   k   a   a   d   y   t   f   t   s   y   w   i

----.----+----.----+----.----+----.----+----.----+

TAGGTTGGGTAAAACAGAGGCCTGGACATGGCCTTGAGTGGATTGGAGAT
----.----+----.----+----.----+----.----+----.----+   150
ATCCAACCCATTTTGTCTCCGGACCTGTACCGGAACTCACCTAACCTCTA g   w   v   k   q   r   p   g   h   g   l   e   w   i   g   d

----.----+----.----+----.----+----.----+----.----+

ATTTACCCTGGAGGTGGTTATACTAATTATAATGGGAAGTTCAGGGGCAA
----.----+----.----+----.----+----.----+----.----+   200
TAAATGGGACCTCCACCAATATGATTAATATTACCCTTCAAGTCCCCGTT i   y   p   g   g   g   y   t   n   y   n   g   k   f   r   g   k

----.----+----.----+----.----+----.----+----.----+

GGCCACACTGACTGCAGACACATCCTCCAGCACAGCCTACATGCAGCTCA
----.----+----.----+----.----+----.----+----.----+   250
CCGGTGTGACTGACGTCTGTGTAGGAGGTCGTGTCGGATGTACGTCGAGT a   t   l   t   a   d   t   s   s   s   t   a   y   m   q   l   s

GCAGCCTGACATCTGAGGACTCTGCCATCTATTATTGTGTAAGAGGAAGG
----.----+----.----+----.----+----.----+----.----+   300
CGTCGGACTGTAGACTCCTGAGACGGTAGATAATAACACATTCTCCTTCC s   l   t   s   e   d   s   a   i   y   y   c   v   r   g   r

----.----+----.----+----.----+----.----+----.----+

TCATATGATTCCGACGGGGAGGGGGACTACTGGGGTCAAGGAACCTCAGT
----.----+----.----+----.----+----.----+----.----+   350
AGTATACTAAGGCTGCCCCTCCCCCTGATGACCCCAGTTCCTTGGAGTCA s   y   d   s   d   g   e   g   d   y   w   g   q   g   t   s   v

----.----+----.----+----.----+----.----+----.----+

CACCGTCTCCTCA
----.----+---   363
GTGGCAGAGGAGT t   v   s   s

```
SAHATYGTGATGACCCAAACTCCACTCTCCCTGCCTGTCAGTCTTGGAGA
----.----+----.----+----.----+----.----+----.----+   50
STDTARCACTACTGGGTTTGAGGTGAGAGGGACGGACAGTCAGAACCTCT
e/d i   v  m  t  q  t  p  l  s  l  p  v  s  l  g  d
q/h

----.----+----.----+----.----+----.----+----.----+

TCAAGCCTCCATCTCTTGT AGATCTAGTCAGACCATTACACACGGTAATG
----.----+----.----+----.----+----.----+----.----+  100
AGTTCGGAGGTAGAGAACA TCTAGATCAGTCTGGTAATGTGTGCCATTAC q   a   s   i   s   c  r  s  s  q  t  i  t  h  g  n  g

----.----+----.----+----.----+----.----+----.----+

GAAACACCTATTTATAT TGGTACCTGCAGAAACCAGGCCAGTCTCCAAAG
----.----+----.----+----.----+----.----+----.----+  150
CTTTGTGGATAAATATA ACCATGGACGTCTTTGGTCCGGTCAGAGGTTTC n   t   y   l   y  w  y  l  q  k  p  g  q  s  p  k

----.----+----.----+----.----+----.----+----.----+

CTCCTGATCTAC AGGGTTTCCAACCGATTTTCT GGGGTCCCAGACAGGTT
----.----+----.----+----.----+----.----+----.----+  200
GAGGACTAGATG TCCCAAAGGTTGGCTAAAAGA CCCCAGGGTCTGTCCAA l   l   i   y  r  v  s  n  r  f  s  g  v  p  d  r  f

----.----+----.----+----.----+----.----+----.----+

CAGTGGCAGTGGATCAGGGACAGATTTCACACTCAAGATCAGCAGAGTGG
----.----+----.----+----.----+----.----+----.----+  250
GTCACCGTCACCTAGTCCCTGTCTAAAGTGTGAGTTCTAGTCGTCTCACC s   g   s   g   s   g   t   d   f   t   l   k   i   s   r   v   e

AGGCTGAGGATATGGGAGTTTATTACTGC TTTCAAGGTACACATGCTCCT
----.----+----.----+----.----+----.----+----.----+  300
TCCGACTCCTATACCCTCAAATAATGACG AAAGTTCCATGTGTACGAGGA a   e   d   m   g   b   y   y   c  f  q  g  t  h  a  p

----.----+----.----+----.----+----.----+----.----+

CGGACG TTCGGTGGAGGCACCAAGCTGGAAATCAAA
----.-+---+----.----+----.----+----.-  336
GCCTGC AAGCCACCTCCGTGGTTCGACCTTTAGTTT r   t  f  g  g  g  t  k  l  e  i  k

----.----+----.----+----.----+----.-
```

RECOMBINANT HUMAN ANTI-LEWIS B ANTIBODIES

The present invention relates to the generation, by recombinant DNA methods, of novel recombinant immunoglobulins specific for the human Lewis b cancer antigen. The invention also discloses methods for the production of these recombinant antibodies, for the diagnosis and treatment of certain human cancers.

Transformation of a normal cell to a malignant cell is often accompanied by a change in the expression of cell surface antigens. These different phenotypes can be detected using monoclonal antibodies specific for such antigens. In this way, different cancer cells can be detected and characterized (Lloyd, K. O. (1983) "Human Tumour Antigens: Detection and Characterization with Monoclonal Antibodies" in R. B. Herberman, ed., Basic and Clinical Tumour Immunology, pp 159–214, Martinus Nijhoff, Boston).

The expression of the Lewis b antigen on cancer and non-cancer cells has been examined. The antigen is expressed on cell lines from colon, lung, bladder, breast, renal, pancreatic and ovarian cancers. The expression of the antigen is greatly increased in cancer tissues as compared to its expression in the corresponding normal tissue. Antibodies to the Lewis b antigen are considered to be useful diagnostic and therapeutic agents (Sakamoto J. et al., (1986) Cancer Research 46, 1553–1561).

Monoclonal antibody 58-1066 is a murine monoclonal antibody that has been raised against the Lewis b antigen. This murine antibody is specific for the Lewis b antigen and exhibits little cross-reactivity with normal cells. This makes the Lewis b antigen a powerful tool for the detection and characterization of particular human cancer types in vitro. However, the in vivo use of murine antibodies as agents for the diagnosis and treatment of human diseases is severely curtailed by a number of factors. Specifically, the human body recognizes murine antibodies as foreign. This can elicit a human anti-mouse antibody (HAMA) response (Schroff, R., et al., (1985) Cancer Res. 45 879–885) which results in rapid clearance of the antibody from the circulation. Furthermore, the Fc portion of a murine antibody is not as efficacious as the human Fc as stimulating human complement or cell-mediated cytotoxicity. For the in vivo use of murine antibodies in diagnosis and therapy, these problems must be circumvented.

EP120694 (Celltech) and EP125023 (Genentech) disclose the development of 'chimeric' antibodies using recombinant DNA methods. Such antibodies comprise the variable regions from one species (eg mouse) and the constant regions from another species (eg human). Such chimeric antibodies have the advantage, that they retain the specificity of the murine antibody but can also stimulate human Fc dependent complement fixation and cell-mediated cytotoxicity. However, the murine variable regions can still elicit a HAMA response (Bruggemann, M. et al., (1989) J. Exp. Med. 170, 2153–2157) thereby limiting the value of chimeric antibodies as diagnostic and therapeutic agents.

British Patent Application Number GB2188638A (Winter) discloses a process whereby recombinant antibodies can be generated by substitution of only the variable region CDRs of one antibody with those from another. Typically, this 'CDR-grafting' technology has been applied to the generation of recombinant, pharmaceutical antibodies consisting of murine CDRs, human variable region frameworks and human constant regions (Reichmann, L. et al., (1988) Nature 332, 323–327). Such 'reshaped' or 'humanized' antibodies have less murine content than chimeric antibodies and retain the human constant regions necessary for the stimulation of human Fc dependent effector functions. In consequence, the humanized antibodies are less likely than chimeric antibodies to evoke a HAMA response when administered to humans, their half-life in circulation should approach that of natural human antibodies and their diagnostic and therapeutic value is enhanced.

In practice, for the generation of efficacious humanized antibodies retaining the specificity of the original murine antibody, it is not usually sufficient simply to substitute CDRs. In addition, there is thought to be a requirement for the inclusion of a small number of critical murine antibody residues in the human variable region so as to retain the specificity of the murine antibody. The identity of these residues depends on the structure of both the original murine antibody and the acceptor human antibody. British Patent Application Number 9019812.8 discloses a method for identifying a minimal number of substitutions of foreign residues sufficient to promote efficacious antigen binding.

The present invention provides novel, humanized monoclonal antibodies specific for the human Lewis b cancer antigen. This has been achieved by the conversion of the murine 58-1066 monoclonal antibody to humanized antibodies by utilizing CDR-grafting technologies. The invention also provides methods for the production of these humanized antibodies to be used in the diagnosis and treatment of certain human cancers.

BRIEF DESCRIPTION OF THE FIGURES

FIG. 1 shows the DNA sequence and corresponding amino acid sequence of the murine 58-1066 heavy chain variable region (VH). The CDRs are boxed. Underlined nucleotides and amino acid residues are derived from the oligonucleotide primers used. The positive strand DNA sequence is (SEQ ID NO: 24). The indicated amino acid sequence is (SEQ ID NO: 25).

FIG. 2 Shows the DNA sequence and corresponding amino acid sequence of the murine 58-1066 light chain variable region (VK). The CDRs are boxed. Underlined nucleotides and amino acid residues are derived from the oligonucleotide primers used. The positive strand DNA sequence is (SEQ ID NO: 26). The indicated amino acid sequence is (SEQ ID NO: 27).

SUMMARY OF THE INVENTION

Figure 3:
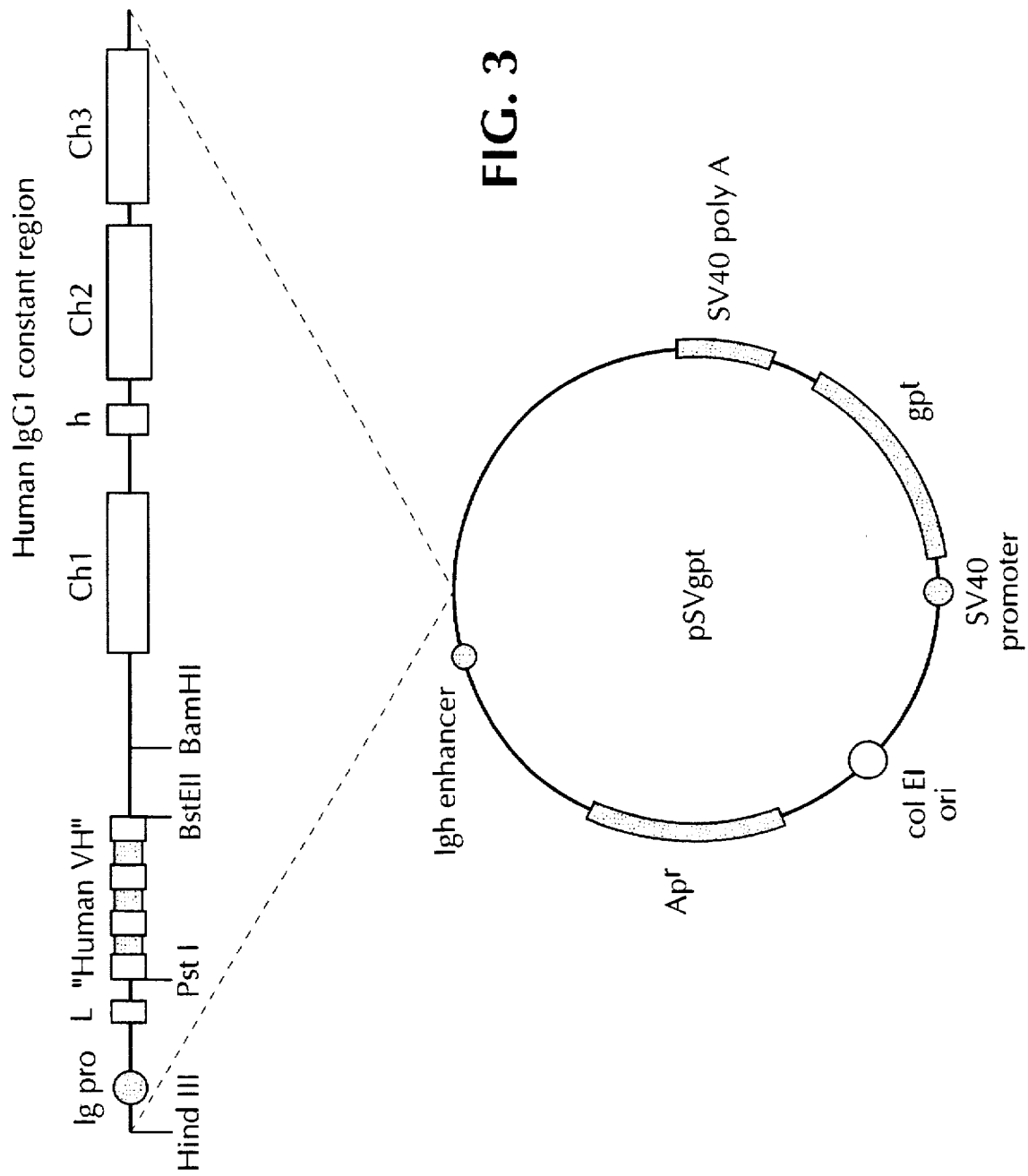
FIG. 3 shows the vector pSVgpt for the expression of chimeric or humanized heavy chains in mammalian cells.
Figure 4:
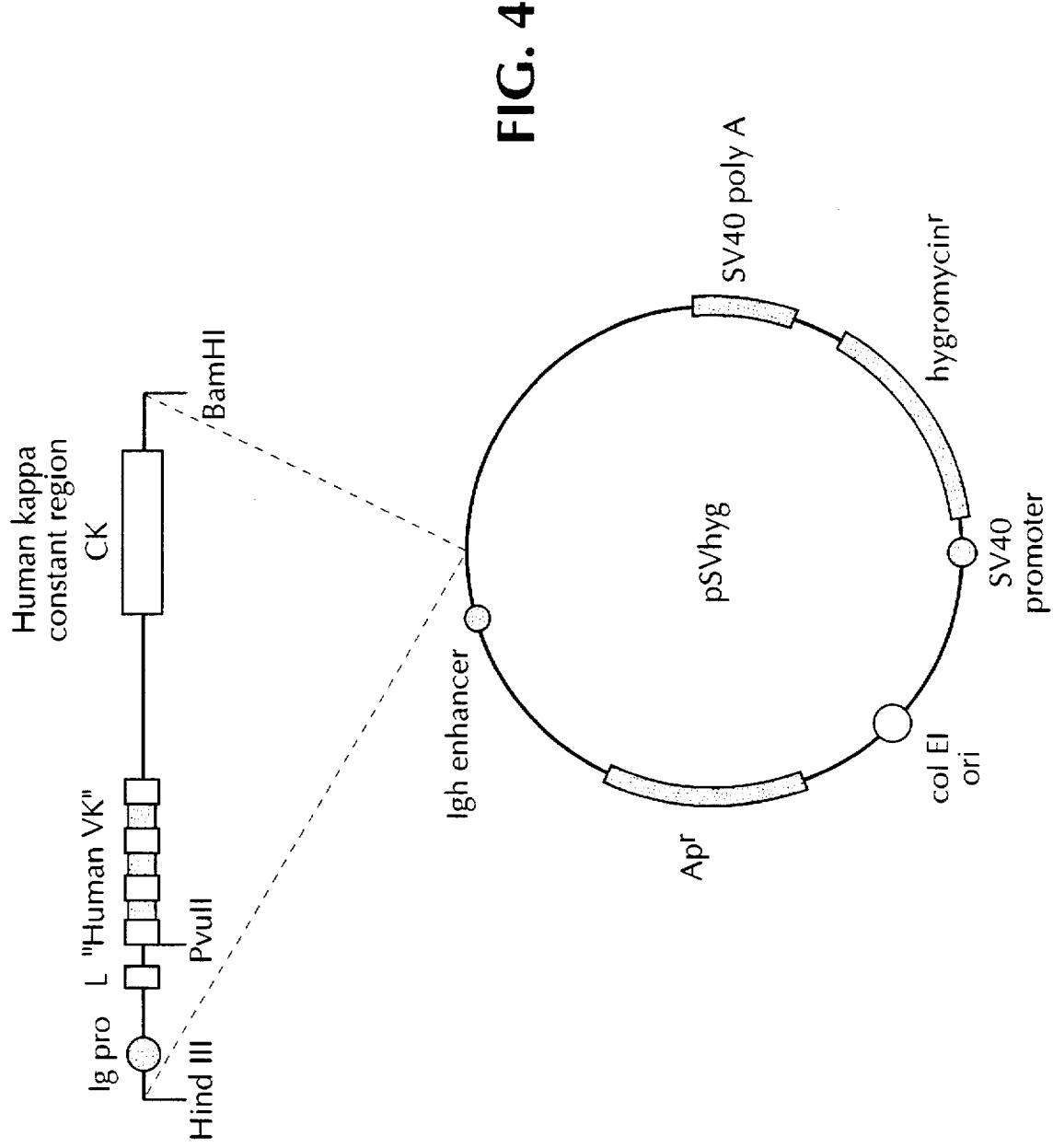
FIG. 4 shows the vector pSVhyg for the expression of chimeric of humanized light chains in mammalian cells.

One aspect of the invention is to provide humanized antibodies specific for the Lewis b antigen.

Another aspect of the invention is to provide polynucleotides encoding humanized antibodies specific for the Lewis b antigen. Various expression vectors comprising polynucleotides encoding humanized Lewis b antigen specific antibodies joined to promoter sequences are also provided. Similarly, another aspect of the invention is host cells transformed with expression vectors for the expression of humanized Lewis b antigen specific antibodies.

Another aspect of the invention is to provide humanized anti-Lewis b antibodies that are labeled with a detectable label or a therapeutic label.

Another aspect of the invention is to provide methods for treating and/or diagnosing cancer by administering a composition comprising a humanized Lewis b antigen specific antibody with or without a therapeutic label. One method of detecting cancer cells involves the steps of administering a labeled antibody (detectable label) to a patient and subsequently detecting where in the body the labeled antibody has bound.

Another aspect of the invnetion is to provide polynucleotides encoding murine antibody 58-1066, as well as vectors and host cells for the recombinat expression of murine antibody 58-1066.

DETAILED DESCRIPTION OF THE SPECIFIC EMBODIMENTS

As used herein, the term "humanized" antibody refers to a molecule that has its CDRs (complementarity determining regions) derived from a non-human species immunoglobulin and the remainder of the antibody molecule derived mainly from a human immunoglobulin. The term "antibody" as used herein, unless indicated otherwise, is used broadly to refer to both antibody molecules and a variety of antibody derived molecules. Such antibody derived molecules comprise at least one variable region (either a heavy chain of light chain variable region) and include molecules such as Fab fragments, Fab' fragments, F(ab')$_2$ fragments, Fabc fragments, Fd fragments, Sc antibodies (single chain antibodies), diabodies, individual antibody light chains, individual antibody heavy chains, chimeric fusions between antibody chains and other molecules, and the like.

The term "conventional molecular biology methods" refers to techniques for manipulating polynucleotides that are well known to the person of ordinary skill in the art of molecular biology. Examples of such well known techniques can be found in *Molecular Cloning: A Laboratory Manual 2nd Edition*, Sambrook et al., Cold Spring Harbor, N.Y. (1989). Examples of conventional molecular biology techniques include, but are not limited to, in vitro ligation, restriction endonuclease digestion, PCR, cellular transformation, hybridization, electrophoresis, DNA sequencing, cell culture, and the like.

The term "variable region" as used herein in reference to immunoglobulin molecules has the ordinary meaning given to the term by the person of ordinary skill in the act of immunology. Both antibody heavy chains and antibody light chains may be divided into a "variable region" and a "constant region". The point of division between a variable region and a heavy region may readily be determined by the person of ordinary skill in the art by reference to standard texts describing antibody structure, e.g., Kabat et al. "Sequences of Proteins of Immunological Interest: 5th Edition" U.S. Department of Health and Human Services, U.S. Government Printing Office (1991).

The present invention provides humanized antibody molecules specific for Lewis b antigen in which at least parts of the CDRs of the heavy and/or light chain variable regions of a human antibody (the receptor antibody) have been substituted by analogous parts of CDRs of a murine monoclonal antibody and the humanized antibody can specifically bind to the same target as the 58-1066 antibody. In a preferred embodiment of the subject invention, the CDR regions of the humanized Lewis b specific antibody are derived from the murine antibody 58–1066. Some of the humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitutions that improve the binding properties of a humanized antibody region that is specific for the same target as the murine antibody 58–1066. A minimal number of substitutions are made to the framework region in order to avoid large-scale introductions of non-human framework residues and to ensure minimal immunogenicity of the humanized antibody in humans. The donor monoclonal antibody of the present invention is the murine antibody 58-1066, which is specific for the human Lewis b antigen.

The humanized antibodies of the present invention include complete antibody molecules having full length heavy and light chains, or any fragment thereof, such as the Fab or (Fab')$_2$ fragments, a heavy chain and light chain dimer, or any minimal fragment thereof such as a Fv, an SCA (single chain antibody), and the like, specific for the Lewis b antigen molecule.

In addition to providing for humanized Lewis b antigen specific antibodies, the subject invention provides for polynucleotides encoding humanized Lewis b antigen specific antibodies. The subject polynucleotides may have a wide variety of sequences because of the degeneracy of the genetic code. A person of ordinary skill in the art may readily change a given polynucleotide sequence encoding a humanized Lewis b antigen specific antibody into a different polynucleotide encoding the same humanized Lewis b antigen specific antibody embodiment. The polynucleotide sequence encoding the antibody may be varied to take into account factors affecting expression such as codon frequency in the host cell of interest, RNA secondary structure, and the like.

The humanized antibodies of the subject invention may be produced by a variety of methods useful for the production of polypeptides, e.g. in vitro synthesis, recombinant DNA production, and the like. Preferably, the humanized antibodies are produced by recombinant DNA technology.

The humanized Lewis b antigen specific antibodies of the invention may be produced using recombinant immunoglobulin expression technology. The recombinant production of immunoglobulin molecules, including humanized antibodies are described in U.S. Pat. No. 4,816,397 (Boss et al.), U.S. Pat. No. 4,816,567 (Cabilly et al.) U.K. patent GB 2,188,638 (Winter et al.), and U.K. patent GB 2,209,757. Techniques for the recombinant expression of immunoglobulins, including humanized immunoglobulins, can also be found, among other places in Goeddel et al., *Gene Expression Technology Methods in Enzymology Vol.* 185 Academic Press (1991), and Borreback, *Antibody Engineering*, W. H. Freeman (1992). Additional information concerning the generation, design, and expression of recombinant antibodies can be found in Mayforth, *Designing Antibodies*, Academic Press, San Diego (1993).

The recombinant humanized anti-Lewis b antibodies of the invention may be produced by the following process or other recombinant protein expression methods:

a. Constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine 58-1066 monoclonal antibody, and the remainder of the antibody is derived from a human immunoglobulin, thereby producing a vector for the expression of a humanized antibody heavy chain.

b. Constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine 58-1066 monoclonal antibody, and the remainder of the antibody is derived from a human immunoglobulin, thereby producing a vector for the expression of humanized antibody light chain.

c. Transferring the expression vectors to a host cell by conventional molecular biology methods to produce a transfected or transformed host cell for the expression of humanized anti-Lewis b antigen antibodies.

d. Culturing the transfected or transformed cell by conventional cell culture techniques so as to produce humanized anti-Lewis b antigen antibodies.

Host cells may be cotransfected with two expression vectors of the invention, the first vector containing an operon encoding a heavy chain derived humanized antibody polypeptide and the second containing an operon encoding a light chain derived humanized antibody polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain derived polypeptide variable regions.

The coding sequences for the heavy and light chains may comprise cDNA or genomic DNA or both.

The host cell used to express the recombinant antibody of the invention may be either a bacterial cell such as *Escherichia coli*, or preferably a eukaryotic cell.

Preferably a mammalian cell such as a Chinese hamster ovary cell, or a myeloma cell such as NSO, SP2/O, or YB2/0 may be used. The choice of expression vector is dependent upon the choice of host cell, and may be selected so as to have the desired expression and regulatory characteristics in the selected host cell.

The general methods for construction of the vector of the invention, transfection of cells to produce the host cell of the invention, culture of cells to produce the antibody of the invention are all conventional molecular biology methods.

Likewise, once produced, the recombinant antibodies of the invention may be purified by standard procedures of the art, including cross-flow filtration, ammonium sulphate precipitation, affinity column chromatography, gel electrophoresis and the like.

The humanized Lewis b antigen specific antibodies of the present invention may be used in conjunction with, or attached to other antibodies (or parts thereof) such as human or humanized monoclonal antibodies. These other antibodies may be reactive with other markers (epitopes) characteristic for the disease against which the antibodies of the invention are directed or may have different specificities chosen, for example, to recruit molecules or cells of the human immune system to the diseased cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labelling the humanized antibodies with labels that produce a detectable signal (either in vitro or in vivo) or with a label having a therapeutic property. Some labels, e.g., radionuclides may produce a detectable signal and have a therapeutic property. Examples of radionuclide labels include $^{125}$I, $^{131}$I, $^{14}$C. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or an agglutination agent, labels which produce an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate, cisplatin, fluorouracil, taxol and the like.

The subject invention also provides for a variety of methods for treating and/or detecting cancer cells. These methods involve the administration of humanized Lewis b antigen specific antibodies, either labelled or unlabelled, to a patient. One method of detecting cancer cells in a human involves the step of administering a labeled humanized Lewis b antigen specific antibody (labelled with a detectable label) to a human and subsequently detecting bound labeled antibody by the presence of the label.

The recombinant antibodies of this invention may also be used for the selection and/or isolation of human monoclonal antibodies, and the design and synthesis of peptide or non-peptide compounds (mimetics) which would be useful for the same diagnostic and therapeutic applications as the antibodies (e.g. Saragovi et al., (1991) *Science* 253:792–795).

When the humanized Lewis b antigen specific antibodies of the invention are used in vivo, the antibodies are typically administered in a composition comprising a pharmaceutical carrier. A pharmaceutical carrier can be any compatible, non-toxic substance suitable for delivery of the monoclonal antibodies to the patient. Sterile water, alcohol, fats, waxes, and inert solids may be included in the carrier.

Pharmaceutically accepted adjuvants (buffering agents, dispersing agent) may also be incorporated into the pharmaceutical composition.

The humanized antibodies compositions of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycerine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference.

The subject invention provide numerous humanized antibodies specific for the Lewis b antigen based on the discovery that the CDR region s of the murine monoclonal antibody could be spliced into a hum an acceptor framework so as to produce a humanized recombinant antibody specific for the Lewis b antigen. Preferred humanized Lewis b antigen specific antibodies contain additional change in the framework region (or in other regions) to increase binding for Lewis b antigen. Particularly preferred embodiments of the invention are the exemplified humanized antibody molecules having superior binding properties for Lewis b antigen.

The following examples are offered by way of illustration of the invention, and should not be interpreted as a limitation of the invention.

EXAMPLES

In the following examples all necessary restriction and modification enzymes, plasmids and other reagents and materials were obtained from commercial sources unless otherwise indicated.

Unless otherwise indicated, all general recombinant DNA methodology was performed as described in "Molecular Cloning, A Laboratory Manual" (1989) Eds J. Sambrook et al., published by Cold Spring Harbor Laboratory Press, Cold Spring Harbor, N.Y.

In the following examples these abbreviations may be employed:

| | |
|---|---|
| dCTP | deoxycytidine triphosphate |
| dATP | deoxyadenosine triphosphate |
| dGTP | deoxyguanosine triphosphate |
| dTTP | deoxythymidine triphosphate |
| DTT | dithiothreitol |
| C | cytosine |
| A | adenine |
| G | guanine |
| T | thymine |
| PBS | phosphate buffered saline |
| PBSB | phosphate buffered saline containing 0.5% (w/v) bovine serum albumin |
| PBST | phosphate buffered saline containing 0.05% (v/v) Tween-20 |
| IL-1 | Interleukin 1 |

EXAMPLE 1 Production Of Humanized Antibodies Specific For The Lewis B Antigen The source of the donor CDRs used to prepare these recombinant antibodies was a murine monoclonal antibody, mAb58-1066, which is specific for the Lewis b antigen of certain human cancers. The 58-1066 monoclonal antibody (IgG3/K) was produced by immunization of CD-1 mice with Lewis b-Tighe plus IL-1 and subsequent production and screening of hybridoma cells. Cytoplasmic RNA was prepared from the mAb 58-1066 hybridoma cell line by the method of Favoloro, J. et al., (1980), Methods in Enzymology, 65, 718–749). cDNA was synthesized using Ig variable region primers as follows: for the Ig heavy chain variable region (VH), the primer CG3FOR (5' TTAAGCT-TAGACAGATCGGGCTGTTGTTGT 3') (SEQ ID NO:1) was used, for the light chain variable region (VK), the primers CK2FOR (5' GGAAGCTTGAAGATGGATA-CAGTTGGTGCAGC 3') (SEQ ID. NO.: 2) and 856 (5' AACCTGCCCGGGACCCCAGAAAAT 3') (SEQ. ID NO.: 3) were used. cDNA synthesis reactions consisted of 5 μg RNA, 20 pmol CG3FOR, 856 or CK2FOR, 250 μM each of dATP, dCTP, dGTP and dTTP, 100 mM TrisHCl pH8.3, 140 mM KCl, 10 mM DTT, 10 mM MgCl$_2$, and 31.5 units of RNase inhibitor (Pharamcia, Milton Keynes, U.K.) in a total volume of 50 μl. Samples were heated to 70° C. for 10 minutes (min) then slowly cooled to 42° C. over a period of 30 minutes. 100 units of Moloney Murine Leukemia virus (M-MLV) reverse transcriptase (Life Technologies Ltd. Paisley, U.K.) was added and incubation at 42° C. continued for 1 hour. VH and VK cDNA were then amplified using the polymerase chain reaction (PCR) as described by Saiki, R. K. et al., (1988), Science, 239, 487–491.

The primers used were:

| | |
|---|---|
| CG3FOR | (5' TTAAGCTTAGACAGATGGGGCTGTTGTTGT 3') |
| | (SEQ ID NO:1) |
| CK2FOR | (5' GGAAGCTTGAAGATGGATACAGTTGGTGCAGC 3')' |
| | (SEQ ID NO:2) |
| 856 | (5' AACCTGCCCGGGACCCCAGAAAAT 3') |
| | (SEQ ID NO:3) |
| VH1BACK | (5' AGGTSMARCTGCAGSAGTCWGG 3') |
| | (SEQ ID NO:4) |
| SK3BACK | (5' ACTAGTCGACATGAGGTKGYYTGYTSGGYTBYTGRKG 3') |
| | (SEQ ID NO:5) |

-continued

VK8BACK (5' CWGAGAAATTCAGCTGACCCAGTCTC 3')

(SEQ ID NO:6)

VK5BACK (5' TTGAATTCGGTGCCAGAKCWSAHATYGTKATG 3')

(SEQ ID NO:7)

where M=C or A, S=C or G, R=A or G, K=G or T, Y=T or C, B=not A, H=not G and W=A or T. Such primers and their use in the PCR amplification of mouse Ig DNA are described by Orlandi, R. et al., (1989), Proc. Natl. Acad. Sci. USA, 86, 3833–3837. For PCR amplification of VH, 5 µl RNA/cDNA hybrid was mixed with 25 pmol CG3FOR and VH1BACK primers. For PCR amplification of VK, 5 µl RNA/cDNA hybrid was mixed with 25 pmol of each of the primers CK2FOR and VK8BACK or 856 and VK5BACK or 856 and SK3BACK. To these mixtures was added 200 µM each of dATP, dCTP, dGTP and dTTP, 67 mM TrisHCl pH8.8, 17 mM (NH$_4$)$_2$SO$_4$, 10 mM MgCl$_2$, 0.02%(w/v) gelatin (1 mM MgSO$_4$ for the VKs) and 2.5 units of AmpliTaq™ DNA polymerase (Perkin Elmer Ltd, Beaconsfield, U.K.) in a total volume of 50 µl. These were then subjected to 25 (or 30 for thyUks) thermal cycles of PCR at 94° C., 30s; 50° C. (or 52° C. for the VKs), 40 s; 72° C., 30 s; ending with 5 min at 72° C. For cloning and sequencing, amplified DNA was purified by electrophoresis in a low melting point agarose gel and by Elutip-d column chromatography (Schleicher and Schuell, Dussel, Germany). Amplified VH DNA was cut with HindIII and PstI and cloned into M13mp18 or M13mp19 cut with HindIII and PstI (Life Technologies Ltd, Paisley, U.K.). Amplified VK DNA was cut with HindIII and PvuII (fragments generated using CK2FOR AND VK8BACK) OR SmaI AND EcoRI (fragments generated using 856 and VK5BACK) or SmaI and SalI (fragments generated using 856 and SK3BACK) and cloned into appropriately cut M13mp18 or M13mp19 (Life Technologies Ltd., Paisley, U.K.)

The resulting clones were sequenced by the dideoxy method (Sanger, F. et al., (1977), Proc. Natl Acad. Sci. USA 74:5463–5467) using Sequenase (United States Biochemical, Cleveland, Ohio, USA). The DNA and protein sequences of the 58-1066 VH and VK domains are shown in FIGS. 1 and 2. The location of the CDRs was determined with reference to Kabat, E. A. et al., (1987) "Sequences of Protein of Immunological Interest", US Department of Health and Human Services, US Government Printing Office, and utilizing computer assisted alignment with other VH and VK sequences.

The transfer of the murine CDRs to human frameworks was achieved by oligonucleotide site-directed mutagenesis, based on the method of Nakamye, K. and Eckstein, F. (1986) Nucleic Acids Res. 14:9679–9698. The human framework regions chosen to receive the transplanted CDRs were NEWM and REI (as defined in Kabat et al. "Sequences of Proteins of Immunological Interest: 5th Edition" and similar publications) for the heavy and light chains respectively. The structures of these proteins have been solved crystallographically. The templates for mutagenesis were human framework region genes containing irrelevant CDRs and consisted of synthetic DNAs cloned into M13 phage (Riechmann, L. et al., (1988) Nature 332:323–327).

The oligonucleotides used were:

NEWM VH:

VHCDR1 5'GGCTGTCTCACCCAACCTATCCAGTAGCTAGTGAAGGTGTAATCAGAAG
CGGTGCAGGTCAGGC 3' (SEQ ID NO: 8)

VHCDR2 5'CAGGCTGAACTGGTTGGAGCTGGTGTCTGCCAGCATTGTCACTCTGCCC
CTGAACTTCCCATTATAATTAGTATAACCACCTCCAGGGTAAATATCTCCA
ATCCACTCAAGACC 3'
(SEQ ID NO: 9)

VHCDR3 5'CCCTTGGCCCCAGTAGTCCCCCTCCCCGTCGGAATCATATGACCTTCCT
CTTACACAATAATAGACCGCGG 3'
(SEQ ID NO: 10)

REI VK:

VKCDR1 5'CCTGGCTTCTGCTGGTACCAATATAAATAGGTGTTTCCATTACCGTGTG
TAATGGTCTGACTAGATCTACAGGTGATGGTCACTCTGTCACCC 3'
(SEQ ID NO: 11)

VKCDR2 5'GCTGAATCTGCTTGGCACACCAGAAAATCGGTTGGAAACCCTGTAGATC
AGCAGCTTTGG3' (SEQ ID NO: 12)

VKCDR3 5'GGTCCCTTGGCCGAACGTCCGAGGAGCATGTGTACCTTGAAAGCAGTAG
TAGGTGGCGATGTCC3' (SEQ ID NO: 13)

A number of additional, murine residues were introduced into the variable region frameworks by extension the CDR primers. Specifically (single letter amino acid code used and Kabat et al numbering):

NEWM V(24) changed to A (NEWM VHCDR1 oligonucleotide)

NEWM G(26) changed to D (NEWM VHCDR1 oligonucleotide)

NEWM S(27) changed to Y (NEWM VHCDR1 oligonucleotide)
NEWM S(30) changed to T (NEWM VHCDR1 oligonucleotide)
NEWM V(71) changed to A (NEWM VHCDR2 oligonucleotide)
NEWM K(75) changed to S (NEWM VHCDR2 oligonucleotide)
NEWM A(93) changed to V (NEWM VHCDR3 oligonucleotide)

From previous data these residues are recognized as important for retaining original antigen specificity. Some possible explanations for their significance in retaining antigen specificity are as follows:

The change of residues NEWM V(24) to the smaller A facilities the accommodation of the heterologous CDR1 loop. The NEWM S(27) to Y change was made because S(27) is an unusual residue in subgroup II human heavy chains (Reichmann et al., (1988) Nature 332, 323–327). Amino acids VH(27–30, 47–49, 71) are residues of the 'vernier zones' as defined by Foote and Winter (Foote, J. and Winter G. (1992) J. Mol. biol. 224, 487–499). These zones are believed to be important for adjusting CDR structures to promote antigen binding. This explanation accounts for the changes NEWM S(27) to Y and NEWM V(71) to A. These explanations are not limitations on the invention. Instead, these explanations for the retention of binding specificity are included in order to provide guidance in designing additional lewis b antigen specific humanized antibodies not explicitly described in these examples.

For site directed mutagenesis the VH and VK oligonucleotides encoding the murine CDRs were phosphorylated with T4 Kinase (Life Technologies Ltd., Paisley, U.K.). A 25 fold molar excess of each of the three VH or VK primers were added to 0.5 μg of appropriate VH or VK single stranded template DNA in M13 (NEWM VH: M13VHPCR1; REI: M13VKPCR2) in 40 mM Tris HCl pH7.5, 20 mM $MgCl_2$, 50 mM NaCl and annealed by heating to 80 C. for a few minutes and slowly cooling to 37° C. In addition oligonucleotides 844 (5'GCTCTGGGTCATCTGGATGTCGG3') (SEQ ID NO: 14) and 850 (5'ATGGTGAAGGTGTAGTCGGTACCGC3') (SEQ ID NO: 15) were treated in the same way and included in the mutagenesis reaction for the VK. These were included to reintroduce the authentic M(4) and Y(71) REI residues into the HuVK (not present in M13VkPCR2). The annealed DNA was extended with 2.5 units of T7 DNA polymerase (cloned, United States Biochemical, Cleveland, Ohio, USA) in a reaction mixture containing 0.5 units of T4 DNA ligase (Life Technologies Ltd., Paisley, U.K.), 0.25 mM of each of dATP, dGTP, dTTP, and dCTP (Pharmacia, Milton Keynes, U.K.), 40 mM Tris HCl pH7.5, 20 mM $MgCl_2$, 50 mM NaCl, 6.5 mM DTT and 1 mM ATP in a total volume of 30 μl. The mixture was incubated at room temperature for 1 h. A 1 μl aliquot of this extension/ligation mixture was then used in an asymmetric PCR for the specific amplification of the newly synthesized strand. The reaction contained 1 μl extension/ligation mixture, 250 μM of each of dATP, dGTP, dTTP and dCTP, 67 mM Tris HCl pH8.8, 17 mM $(NH_4)_2SO_4$, 10 mM $MgCl_2$, 0.02% (w/v) gelatin, 10 Units of AmpliTaq DNA polymerase and 25 pmol of appropriate oligonucleotide primer (5'AACAGCTATGACCATG 3' (SEQ ID NO: 16) for NEWM VH; 5'CTCTCTCAGGGCCAGGCGGTGA 3' (SEQ ID NO: 17) for REI VK) in a total volume of 50 μl. The reaction mixtures were subjected to 30 thermal cycles of PCR at 94° C., 30 s, 55° C., 30 s; 75° C., 1 min ending with 75° C., 5 min. The newly synthesized strand was then amplified by adding 25 pmol of appropriate oligonucleotide primer (5' GTAAAACGACGGCCAGT 3' (SEQ ID NO: 18) for NEWM VH and 5' GCGGGCCTCTTCGCTATTACGC 3' for REI VK) (SEQ ID NO: 20) and adjusting the reaction mixture to include a further 5 nmols of each of dATP, dGTP, dTTP and dCTP and 10 Units of AmpliTaq™. The reactions were subjected to a further 20 PCR cycles as above. The amplified VH and VK DNAs were purified from 1.5% w/v low melting point agarose gels by elutip-d column chromatography. Purified DNA was digested with HindIII and BamHI plus Rsa I (for VHs). BstXI (for VKs) (all restriction enzymes for life technologies Ltd., Paisley, U.K.). There is an RsaI site in the parental VHPCR1 and a BstXI site in the parental VKPCR2, but these sites are deleted during mutagenesis. These digestions therefore select for newly synthesized DNA. The HindIII/BamHI digested VH and VK DNAs were ligated into HindIII/BamHI cut M13mp18 or M13mp19 (both from Pharmacia, Milton Keynes, U.K.) and transformed into competent *E. coli* TG1 (Amersham International Plf, Amersham, U.K.). Single stranded DNA was prepared from individual 'plaques' and sequenced by the dideoxy method using Sequenase (United States Biochemical, Cleveland, Ohio, USA) according to Manufacturer's instructions. Triple CDR mutants were identified in this way and selected for construction of VH and VK expression vectors.

The expression vectors for the humanized VH and VK genes, pSVgpt and pSVhyg are shown in FIGS. 3 and 4. The humanized VH genes, together with the immunoglobulin heavy chain promoter, appropriate splice sites and signal peptide sequences were excised from the M13 clones with HindIII and BamHI and ligated into the heavy chain expression vector, pSVgpt. This vector contains the murine heavy chain immunoglobulin enhancer, the gpt gene under control of the SV40 promoter/enhancer for selection in mammalian cells, the human IgG1 constant region domain and sequences for replication and selection in *E. coli*. The humanized VK gene was cloned into the light chain expression vector pSVhyg in the same way. All features of pSVhyg are the same as in pSVgpt except that the gpt gene is replaced by the gene for hygromycin resistance (hyg) and a human kappa constant region is included instead of the IgG1 constant region.

For transfection into mammalian cells 10 μg of the heavy chain expression vector DNA and 20 μg of the light chain vector DNA were linearized by digestion with PvuI (Life Technologies Ltd, Paisley, U.K.), co-precipitated with ethanol and redissolved in 20 μl of water. The recipient cell line was NSO, a non-immunoglobulin producing mouse myeloma, obtained from the European Collection of Animal Cell Cultures, Porton, U.K., ECAC No. 85110505 cells were grown in Dulbecco's Modified Eagle's Medium supplemented with 10% foetal calf serum and antibiotics (DMEM) (Life Technologies Ltd, Paisley, U.K.). Approximately $10^7$ NSO cells were harvested by centrifugation and resuspended in 0.5 ml DMEM, the digested DNA was added and the cells transferred to a cuvette and placed on ice for 5 min. A single pulse of 170 volts, 960μ farads was administered (Genepulser, BioRad, Richmond, Calif., U.S.A.). After a further 30 min on ice the cells were replaced in a flask in 20 ml DMEM and allowed to recover for 24 hours. After this time the cells were distributed into a 24 well plate in selective medium (DMEM with 0.8 μg/ml mycophenolic acid and 250 μg/ml xanthine). After 3 to 4 days the medium was changed for fresh selective medium. Colonies of transfected cells were visible after 10 to 14 days.

The production of human antibody in the wells containing transfected clones was measured by ELISA. Capture antibody, goat anti-human IgG, gamma chain specific (Sera-Lab Ltd, Crawley Down, U.K.) was diluted to 5 μg/ml in 50 mM carbonate buffer pH9.6, and used to coat polystyrene ELISA plates (Dynatech Immulon 1), 200 μl per well, overnight at 4° C. After washing 3 times with PEST, 50–100 μl of the culture medium to be screened was added to the wells and incubated at 37° C. for 60 min. The wells were washed again with PBST and the reporter antibody, peroxidase-conjugated goat anti-human IgG, gamma chain specific (Sera-Lab Ltd, Crawley Down, U.K.) or peroxidase-conjugated goat anti-human kappa chain (Sera-Lab Ltd, Crawley Down, U.K) was added at 100 ng per well and the plate incubated for a further 60 min. The plate was washed as before then the color was developed. Substrate buffer was prepared by mixing 100 mM citric acid and 100 mM disodium hydrogen phosphate to pH5.0. 25 mg of o-phenylenediamine was dissolved in 50 ml and 5 µl of 30% hydrogen peroxide added just before use. 200 µl was dispensed per well and incubated at room temperature in the dark. The reaction was stopped by addition of 50 µl per well of 12.5% sulphuric acid and the absorbances were read at 492 nm.

Positive cell clones were expanded for antibody purification. For the final expansion to production volume the cells were diluted in DMEM containing 10% IgG-free fetal calf serum. For small scale purification 500 ml of conditioned medium from static flask or spinner cultures was harvested by centrifugation. 0.1 volumes of 1.0M TrisHCl pH8.0 and 0.5 to 1.0 ml of Protein A-agarose (Boehringer Mannheim, Lewes, U.K.) were added. This was stirred overnight at room temperature then collected on a disposable column. This was washed with 10 column volumes of 0.1M TrisHCl pH8.0, 10 column volumes of 0.01M TrisHCl pH8.0 and eluted with 0.1M glycine buffer, pH3.0. 1.0 ml fractions were collected into tubes containing 100 µl of 1.0M TrisHCl, pH8.0. Fractions containing antibody were pooled and dialysed against PBS. The concentrations of the antibody preparations were determined using a Micro BCA Protein Assay Reagent Kit (Pierce, Rockford, USA). Samples were checked by running on 10% SDS-polyacrylamide gels. The amino acid sequences of the variable regions of humanized 58-1066 heavy chain (58-1066 HuVH) and humanized 58-1066 light chain (58-1066 HuVK) are provided in Table 1.

Table 1 shows the variable region sequences of 58-1066 HuVH and 58-1066 HuVK. Murine framework residues are shown in lower case. Some framework residues in NEWM and REI are unusual for human subgroup II heavy chains or human subgroup I kappa chains, respectively, these have been replaced by the residues commonly found at these positions and are underlined in the table.

EXAMPLE 2 Specific Binding of the Humanized 58-1066 Antibody by Synthetic Lewis B Antigen A humanized antibody has been constructed consisting of the humanized heavy chain with the humanized light chain. The humanized antibody shows greater binding efficacy to the synthetic Lewis b antigen than the murine antibody.

The recombinant antibody 58-1066 HuVH/HuVK has been tested in ELISAs using the synthetic Lewis b antigen. The ELISA method is as follows.

Terasaki plates (Nunc, 60 well) were coated with synthetic Lewis b antigen conjugated to human serum albumin (Accurate Chemical and Scientific Corp. N.Y.). T his was achieved by adding 10 µl of a 1 µg/ml antigen solution to each well and leaving the plates to dry overnight. Plates were blocked by adding PBS, 3% w/v BSA) and incubating at room temperature for 1 hour. Plates were washed twice with PBS and antibody (serially diluted in PBA, 3% w/v BSA) added to the wells and incubation carried out for 2 hours at room temperature. Plates were washed 3 times with PBS and bound antibody detected by application of alkaline phosphatase conjugated detection antibody (either rabbit anti-mouse IgG+A+M (H+L) (Zymed) or goat anti-human IgG(Fc) (Coppel), for mouse or humanized antibodies, respectively, diluted 1:400 and 1:1000, respectively in PBS, 3% w/v BSA) Unbound detection antibody was removed by 3 washes with PBS and color developed using phosphatase substrate (Sigma), according to the manufacturer's instructions. Optical density (OD) was measured at 405 nm. Other Lewis related antigens were assayed in a similar way. The Results from these ELISAs are presented in Table 2 below.

TABLE 1

58-1066 HuVH:
QVQLQESGPGLVRPSQTLSLTCTaSdyTFtSYWIGWVRQPPGRGLEWIGDIYPGGGYTNYN
GKFRGRVTMLaDTSsNQFSLRLSSVTAADTAVYYCvRGRSYDSDGEGDYWGQGTTVTVSS
(SEQ ID NO: 20)

58-1066 HuVK:
DIQMTQSPSSLSASVGDRVTITCRSSQTITHGNGNTYLYWYQQKPGKAPKLLIYRVSNRFS
GVPSRFSGSGSGTDYTFTISSLQPEDIATYYCFQGTHAPRTFGQGTKVEIK
(SEQ ID NO: 22)

TABLE 2

| | ELISA (the reactivity against synthetic antigens) | | | | | | | |
|---|---|---|---|---|---|---|---|---|
| | Le$^b$ | Le$^a$ | Le$^y$ | Le$^x$ | H type 2 | Y-backbone | ALe$^b$ | A type 1 |
| Murine 58-1066 | 0.025 | 1.56 | 0.39 | 3.13 | 1.56 | 6.25 | 1.56 | 1.56 µg/ml |
| Humanized 58-1066 | 0.0063 | 100 | 6.25 | 100 | 100 | 100 | 100 | 100 | minimum antibody concentration (µg/ml) which shows positive (O.D. 405 nm > 0.6)

In these ELISAs the HuVH/HuVK humanized 58-1066 antibody is shown to bind to Lewis b antigen 4 fold better than the murine antibody and to be more specific for the Lewis b antigen (i.e., there is less cross reactivity with other Lewis-related antigens than exhibited by the murine antibody).

These test data indicate that the humanized antibody exhibits high affinity and specificity for the Lewis b antigen. Such a humanized antibody (of which the HuVH/HuVK is an example) therefore provides novel, recombinant antibody molecules for the diagnosis and therapy of human cancers characterized by the expression of the Lewis b antigen.

Biological Deposits

On Mar. 11, 1994 Applicants have deposited with the American Type Culture Collection, Rockville, Md., USA (ATCC) the an NSO cell line producing HuVH/HuVK, under ATCC accession no. CRL 11572. This deposit was made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Incorporation By Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

---

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 30 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

TTAAGCTTAG ACAGATGGGG CTGTTGTTGT  30

( 2 ) INFORMATION FOR SEQ ID NO:2:

( i ) SEQUENCE CHARACTERISTICS:
( A ) LENGTH: 32 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:2:

```
GGAAGCTTGA AGATGGATAC AGTTGGTGCA GC                                    32
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
AACCTGCCCG GGACCCCAGA AAAT                                             24
```

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

```
AGGTSMARCT GCAGSAGTCW GG                                               22
```

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

```
ACTAGTCGAC ATGAGGTKGY YTGYTSGGYT BYTGRKG                               37
```

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:6:

```
CWGAGAAATT CAGCTGACCC AGTCTC                                           26
```

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:7:

```
TTGAATTCGG TGCCAGAKCW SAHATYGTKA TG                                    32
```

( 2 ) INFORMATION FOR SEQ ID NO:8:

( i ) SEQUENCE CHARACTERISTICS:
  ( A ) LENGTH: 64 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:8:

GGCTGTCTCA CCCAACCTAT CCAGTAGCTA GTGAAGGTGT AATCAGAAGC GGTGCAGGTC    60

AGGC    64

( 2 ) INFORMATION FOR SEQ ID NO:9:

( i ) SEQUENCE CHARACTERISTICS:
  ( A ) LENGTH: 114 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:9:

CAGGCTGAAC TGGTTGGAGC TGGTGTCTGC CAGCATTGTC ACTCTGCCCC TGAACTTCCC    60

ATTATAATTA GTATAACCAC CTCCAGGGTA AATATCTCCA ATCCACTCAA GACC    114

( 2 ) INFORMATION FOR SEQ ID NO:10:

( i ) SEQUENCE CHARACTERISTICS:
  ( A ) LENGTH: 71 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:10:

CCCTTGGCCC CAGTAGTCCC CCTCCCCGTC GGAATCATAT GACCTTCCTC TTACACAATA    60

ATAGACCGCG G    71

( 2 ) INFORMATION FOR SEQ ID NO:11:

( i ) SEQUENCE CHARACTERISTICS:
  ( A ) LENGTH: 93 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:11:

CCTGGCTTCT GCTGGTACCA ATATAAATAG GTGTTTCCAT TACCGTGTGT AATGGTCTGA    60

CTAGATCTAC AGGTGATGGT CACTCTGTCA CCC    93

( 2 ) INFORMATION FOR SEQ ID NO:12:

( i ) SEQUENCE CHARACTERISTICS:
  ( A ) LENGTH: 60 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:12:

GCTGAATCTG CTTGGCACAC CAGAAAATCG GTTGGAAACC CTGTAGATCA GCAGCTTTGG    60

( 2 ) INFORMATION FOR SEQ ID NO:13:

( i ) SEQUENCE CHARACTERISTICS:
        ( A ) LENGTH: 64 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

```
GGTCCCTTGG CCGAACGTCC GAGGAGCATG TGTACCTTGA AAGCAGTAGT AGGTGGCGAT    60

GTCC                                                                 64
```

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

```
GCTCTGGGTC ATCTGGATGT CGG                                            23
```

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

```
ATGGTGAAGG TGTAGTCGGT ACCGC                                          25
```

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

```
AACAGCTATG ACCATG                                                    16
```

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

```
CTCTCTCAGG GCCAGGCGGT GA                                             22
```

( 2 ) INFORMATION FOR SEQ ID NO:18:

( i ) SEQUENCE CHARACTERISTICS:
    ( A ) LENGTH: 17 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:18:

GTAAAACGAC GGCCAGT                                                17

( 2 ) INFORMATION FOR SEQ ID NO:19:

( i ) SEQUENCE CHARACTERISTICS:
    ( A ) LENGTH: 22 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:19:

GCGGGCCTCT TCGCTATTAC GC                                 22

( 2 ) INFORMATION FOR SEQ ID NO:20:

( i ) SEQUENCE CHARACTERISTICS:
    ( A ) LENGTH: 121 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:20:

```
Gln  Val  Gln  Leu  Gln  Glu  Ser  Gly  Pro  Gly  Leu  Val  Arg  Pro  Ser  Gln
 1                   5                        10                       15

Thr  Leu  Ser  Leu  Thr  Cys  Thr  Ala  Ser  Asp  Tyr  Thr  Phe  Thr  Ser  Tyr
               20                        25                       30

Trp  Ile  Gly  Trp  Val  Arg  Gln  Pro  Pro  Gly  Arg  Gly  Leu  Glu  Trp  Ile
          35                        40                       45

Gly  Asp  Ile  Tyr  Pro  Gly  Gly  Gly  Tyr  Thr  Asn  Tyr  Asn  Gly  Lys  Phe
     50                        55                       60

Arg  Gly  Arg  Val  Thr  Met  Leu  Ala  Asp  Thr  Ser  Ser  Asn  Gln  Phe  Ser
65                        70                       75                       80

Leu  Arg  Leu  Ser  Ser  Val  Thr  Ala  Ala  Asp  Thr  Ala  Val  Tyr  Tyr  Cys
               85                        90                       95

Val  Arg  Gly  Arg  Ser  Tyr  Asp  Ser  Asp  Gly  Glu  Gly  Asp  Tyr  Trp  Gly
          100                       105                      110

Gln  Gly  Thr  Thr  Val  Thr  Val  Ser  Ser
               115                      120
```

( 2 ) INFORMATION FOR SEQ ID NO:21:

( i ) SEQUENCE CHARACTERISTICS:
    ( A ) LENGTH: 112 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:21:

```
Asp  Ile  Gln  Met  Thr  Gln  Ser  Pro  Ser  Ser  Leu  Ser  Ala  Ser  Val  Gly
 1                   5                        10                       15
```

| | | | | | | | | | | | | | |
|---|---|---|---|---|---|---|---|---|---|---|---|---|---|
| Asp | Arg | Val | Thr 20 | Ile | Thr | Cys | Arg | Ser 25 | Gln | Thr | Ile | Thr 30 | His | Gly |
| Asn | Gly | Asn 35 | Thr | Tyr | Leu | Tyr | Trp 40 | Tyr | Gln | Gln | Lys 45 | Pro | Gly | Lys | Ala |
| Pro | Lys 50 | Leu | Leu | Ile | Tyr | Arg 55 | Val | Ser | Asn | Arg | Phe 60 | Ser | Gly | Val | Pro |
| Ser 65 | Arg | Phe | Ser | Gly | Ser 70 | Gly | Ser | Gly | Thr | Asp 75 | Tyr | Thr | Phe | Thr | Ile 80 |
| Ser | Ser | Leu | Gln | Pro 85 | Glu | Asp | Ile | Ala | Thr 90 | Tyr | Tyr | Cys | Phe | Gln 95 | Gly |
| Thr | His | Ala | Pro 100 | Arg | Thr | Phe | Gly | Gln 105 | Gly | Thr | Lys | Val | Glu 110 | Ile | Lys |

( 2 ) INFORMATION FOR SEQ ID NO:22:

( i ) SEQUENCE CHARACTERISTICS:
        ( A ) LENGTH: 965 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:22:

```
CAGGTSMARC  TGCAGSAGTC  WGGAGCTGAG  CTGGTAAGGC  CTGGGACTTC  AGTGAAGATG    60
TCCTGCAAGG  CTGCTGATTA  CACCTTCACT  AGCTACTGGA  TAGGTTGGGT  AAAACAGAGG   120
CCTGGACATG  GCCTTGAGTG  GATTGGAGAT  ATTTACCCTG  GAGGTGGTTA  TACTAATTAT   180
AATGGGAAGT  TCAGGGGCAA  GGCCACACTG  ACTGCAGACA  CATCCTCCAG  CACAGCCTAC   240
ATGCAGCTCA  GCAGCCTGAC  ATCTGAGGAC  TCTGCCATCT  ATTATTGTGT  AAGAGGAAGG   300
TCATATGATT  CCGACGGGGA  GGGGGACTAC  TGGGGTCAAG  GAACCTCAGT  CACCGTCTCC   360
TCAGURSAHA  TYGTGATGAC  CCAAACTCCA  CTCTCCCTGC  CTGTCAGTCT  TGGAGADVMT   420
TSVSGDHTCA  AGCCTCCATC  TCTTGTAGAT  CTAGTCAGAC  CATTACACAC  GGTAATGASS   480
CRSSTTHGNG  GAAACACCTA  TTTATATTGG  TACCTGCAGA  AACCAGGCCA  GTCTCCAAAG   540
NTYYWYKGSK  CTCCTGATCT  ACAGGGTTTC  CAACCGATTT  TCTGGGGTCC  CAGACAGGTT   600
YRVSNRSGVD  RCAGTGGCAG  TGGATCAGGG  ACAGATTTCA  CACTCAAGAT  CAGCAGAGTG   660
GSGSGSGTDT  KSRVAGGCTG  AGGATATGGG  AGTTTATTAC  TGCTTTCAAG  GTACACATGC   720
TCCTADMGVY  YCGTHACGGA  CGTTCGGTGG  AGGCACCAAG  CTGGAAATCA  AARTGGGTKK   780
GURHUVHVSG  GVRSTSTCTA  SDYTTSYWGW  VRGRGWGDYG  GGYTNYNGKR  GRVTMADTSS   840
NSRSSVTAAD  TAVYYCVRGR  SYDSDGGDYW  GGTTVTVSSH  UVKDMTSSSS  ASVGDRVTTC   900
RSSTTHGNGN  TYYWYKGKAK  YRVSNRSGVS  RSGSGSGTDY  TTSSDATYYC  GTHARTGGTK   960
VKGUR                                                                    965
```

( 2 ) INFORMATION FOR SEQ ID NO:23:

( i ) SEQUENCE CHARACTERISTICS:
        ( A ) LENGTH: 121 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..2
        ( D ) OTHER INFORMATION: /note= "Where Xaa=Lys or Gln"

(ix) FEATURE:
  (A) NAME/KEY: Protein
  (B) LOCATION: 4..5
  (D) OTHER INFORMATION: /note= "Where Xaa=Asp or His"

(xi) SEQUENCE DESCRIPTION: SEQ ID NO:23:

```
Gln Val Xaa Leu Gln Xaa Ser Gly Ala Glu Leu Val Arg Pro Gly Thr
         1               5                       10
Ser Val Lys Met Ser Cys Lys Ala Ala Asp Tyr Thr Phe Thr Ser Tyr
 15                  20                  25                   30
Trp Ile Gly Trp Val Lys Gln Arg Pro Gly His Gly Leu Glu Trp Ile
                 35                  40                   45
Gly Asp Ile Tyr Pro Gly Gly Gly Tyr Thr Asn Tyr Asn Gly Lys Phe
             50                  55                  60
Arg Gly Lys Ala Thr Leu Thr Ala Asp Thr Ser Ser Ser Thr Ala Tyr
         65                  70                  75
Met Gln Leu Ser Ser Leu Thr Ser Glu Asp Ser Ala Ile Tyr Tyr Cys
     80                  85                  90
Val Arg Gly Arg Ser Tyr Asp Ser Asp Gly Glu Gly Asp Tyr Trp Gly
 95                 100                 105                  110
Gln Gly Thr Ser Val Thr Val Ser Ser
             115
```

(2) INFORMATION FOR SEQ ID NO:24:

(i) SEQUENCE CHARACTERISTICS:
    (A) LENGTH: 336 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:24:

```
SAHATYGTGA TGACCCAAAC TCCACTCTCC CTGCCTGTCA GTCTTGGAGA TCAAGCCTCC    60
ATCTCTTGTA GATCTAGTCA GACCATTACA CACGGTAATG GAAACACCTA TTTATATTGG   120
TACCTGCAGA AACCAGGCCA GTCTCCAAAG CTCCTGATCT ACAGGGTTTC CAACCGATTT   180
TCTGGGGTCC CAGACAGGTT CAGTGGCAGT GGATCAGGGA CAGATTTCAC ACTCAAGATC   240
AGCAGAGTGG AGGCTGAGGA TATGGGAGTT TATTACTGCT TTCAAGGTAC ACATGCTCCT   300
CGGACGTTCG GTGGAGGCAC CAAGCTGGAA ATCAAA                             336
```

(2) INFORMATION FOR SEQ ID NO:25:

(i) SEQUENCE CHARACTERISTICS:
    (A) LENGTH: 112 amino acids
    (B) TYPE: amino acid
    (C) STRANDEDNESS: unknown
    (D) TOPOLOGY: unknown (ii) MOLECULE TYPE: protein (ix) FEATURE:
    (A) NAME/KEY: Modified-site
    (B) LOCATION: 1..2
    (D) OTHER INFORMATION: /note= "Where Xaa=Glu or Asp"

(ix) FEATURE:
    (A) NAME/KEY: Modified-site
    (B) LOCATION: 17..18
    (D) OTHER INFORMATION: /note= "Where Xaa=Gln or His"

(xi) SEQUENCE DESCRIPTION: SEQ ID NO:25:

-continued

| Xaa 1 | Val | Met | Thr | Gln 5 | Thr | Pro | Leu | Ser | Leu 10 | Pro | Val | Ser | Leu | Gly 15 | Asp |
| Xaa | Gln | Ala | Ser 20 | Ile | Ser | Cys | Arg | Ser 25 | Ser | Gln | Thr | Ile | Thr 30 | His | Gly |
| Asn | Gly | Asn 35 | Thr | Tyr | Leu | Tyr | Trp 40 | Tyr | Leu | Gln | Lys | Pro 45 | Gly | Gln | Ser |
| Pro | Lys 50 | Leu | Leu | Ile | Tyr | Arg 55 | Val | Ser | Asn | Arg | Phe 60 | Ser | Gly | Val | Pro |
| Asp 65 | Arg | Phe | Ser | Gly | Ser 70 | Gly | Ser | Gly | Thr | Asp 75 | Phe | Thr | Leu | Lys | Ile 80 |
| Ser | Arg | Val | Glu | Ala 85 | Glu | Asp | Met | Gly | Val 90 | Tyr | Tyr | Cys | Phe | Gln 95 | Gly |
| Thr | His | Ala | Pro 100 | Arg | Thr | Phe | Gly | Gly 105 | Gly | Thr | Lys | Leu | Glu 110 | Ile | Lys |

What is claimed is:

1. A humanized antibody which specifically binds to a Lewis B antigen, comprising a humanized variable region having a heavy chain region and a light chain region, said heavy chain region having an amino acid sequence as set forth in SEQ ID NO: 20, and said light chain region having an amino acid sequence as set forth in SEQ ID NO: 21.

2. A labeled antibody comprising an antibody according to claim 1 and a detectable label.

3. A polypeptide having an amino acid sequence selected from the group consisting of SEQ ID NOS: 20 and 21.

4. The polypeptide according to claim 3, wherein said polypeptide has the amino acid sequence as set forth in SEQ ID NO: 20.

5. The polypeptide according to claim 3, wherein said polypeptide has the amino acid sequence as set forth in SEQ ID NO: 21.

* * * * *

UNITED STATES PATENT AND TRADEMARK OFFICE
CERTIFICATE OF CORRECTION

PATENT NO. : 5,795,961
DATED : Aug. 18, 1998
INVENTOR(S) : Wallace, et al.

It is certified that error appears in the above-identified patent and that said Letters Patent is hereby corrected as shown below:

In column 7, line 10, "region s" should read as -- regions --.
In column 7, line 11, "hum an" should read as -- human --.
In column 12, line 1, "(SEQ ID NO: 20)" should read as -- (SEQ ID NO: 19) --.
In column 13, last line, "(SEQ ID NO: 22)" should read as
-- (SEQ ID NO: 21) --.

Signed and Sealed this

Twentieth Day of June, 2000

Attest:

Q. TODD DICKINSON

*Attesting Officer*   *Director of Patents and Trademarks*